United States Patent [19]

Spranza, III

[11] Patent Number: 5,013,318

[45] Date of Patent: May 7, 1991

[54] MEDICAL INSTRUMENT FOR MEASURING DEPTH OF FASTENER HOLD IN BONE

[75] Inventor: Joseph J. Spranza, III, Grass Valley, Calif.

[73] Assignee: Special Devices Incorporated, Grass Valley, Calif.

[21] Appl. No.: 560,871

[22] Filed: Jul. 31, 1990

[51] Int. Cl.$^5$ .......................... A61F 5/04; A61B 1/00
[52] U.S. Cl. ....................................... 606/102; 33/512
[58] Field of Search ................. 606/102, 138, 103, 96,
606/97, 99, 100, 205, 206, 207; 33/511, 512,
810, 811, 836, 542

[56] References Cited

U.S. PATENT DOCUMENTS

| | | | |
|---|---|---|---|
| 1,528,273 | 3/1925 | Shwe | 33/512 |
| 1,804,064 | 5/1931 | Sison | 33/512 |
| 1,856,295 | 5/1932 | Sovatkin | 33/512 |
| 1,953,498 | 4/1934 | Pieri | 33/512 |
| 3,740,779 | 6/1973 | Rubricuis | 33/512 |
| 4,294,264 | 10/1981 | Fischell | 33/512 |

Primary Examiner—Robert A. Hafer
Assistant Examiner—Michael Brown

[57] ABSTRACT

A medical instrument for measuring depth of fastener hole in bone. The depth gauge has a scale tube which fits into fastener hole in bone. The zero index of scale tube expands exclusively in radial dimension to a diameter greater than the hole diameter, affording a positive stop for the zero index, thus insuring precise alignment of scale zero index with edge of hole in distal bone wall. A sliding scale marker is frictionally mounted to scale tube, affording a record of the measurement.

11 Claims, 3 Drawing Sheets

MEDICAL INSTRUMENT FOR MEASURING DEPTH OF FASTENER HOLD IN BONE

BACKGROUND—FIELD OF INVENTION

This invention relates to measuring instruments, especially to medical instruments used for measuring the depth of holes in bones for which it is necessary to select fasteners of the correct length.

BACKGROUND—DESCRIPTION OF PRIOR ART

When bones are fractured, it is often necessary to relationally fix (positionally maintain) them with pins, which pins may be either plain or threaded. In practice the bone pieces are suitably and properly arranged, and then a hole is made in the pieces and a pin or screw is inserted into this hole, fastening the pieces together. Subsequently, as required, additional holes are made, and additional fasteners are inserted, to preclude relative movement between the bone pieces. It is necessary for the fractured surfaces to be in close, well aligned contact, to facilitate healing.

It will be apparent that the fasteners must be of the proper length; too short will result in weak fastening, and too long will result in a fastener protruding from the bone into the surrounding tissue. It will also be appreciated that a number of fasteners may be required. Since bones are of varying dimensions, these fasteners will be of various lengths. The surgeon therefore finds it necessary to measure the depth of most of these holes. All of these measurements are done during the procedure, in the operating room, with the patient under anesthetic, which conditions call for spending as little time as necessary. Since time is critical, and precision is also critical, the measurement of these holes must be quick, accurate and convenient.

Heretofore, the instruments available to orthopedic surgeons for measuring the depth of holes in bones had a single hook on one end of a calibrated rod. The surgeon inserted the rod into and thru the hole, and "fished", with the hook for the edge of the hole where it emerged thru the opposite (distal) wall. The hook was fashioned on the end of the rod such that the distal edge of the hole could be "caught," as in using a grapple. Surgeons regarded this type of instrument as unsatisfactory for measuring the depth of the hole because hooking the edge of the hole thru the far wall could be quite difficult. It could also be very uncertain. Because of blood and tissue, vision is impaired during such a proceedure. The bone pieces may be free to move relative to each other. Bone is a porous material, due to the presence of Haversian canals, Volkmann's canals, Lacunae, etc. When fishing with a single hook, it is easy to catch the hook in some porosity in the bone and mistake this for hooking the distal wall. This results in a measurement which is too small. It is also possible to hook tissue the other side of the bone. This results in a measurement which is too large.

Another instrument was proposed, which instrument comprised a pair of axially extending wire hooks. Due to the concept of this instrument, it was unacceptably long. The concept of axially extending wires requires a "storage" place for the wires in the handle of the instrument. This "storage" place is essentially the length of the range of measurement of the instrument. When added together, the range of the instrument plus the length of the "storage" plus the actuating mechanism, the total length is prohibitive. A surgeon would not be able to use such a long instrument in a number of places on and in the human body. It simply would not fit. Further, the instrument under discussion was quite large and heavy. It would be inconvenient to use. Additionally, the instrument was very complex, with many specialized parts. It is widely recognized that an increase in the number of parts means an increase in cost and a decrease in reliability. More parts means higher manufacturing costs and greater maintenance costs. The instrument was not widely accepted, and is not on the market.

A further instrument was described for measuring the depth of a hole in bone. This instrument requires the use of Xray to determine the measurement, and therefore would not be generally applicable.

Surgeons, therefore, have found it increasingly desireable to have an instrument which will provide a quick, precise and convenient method of measuring the depth of holes in bones.

OBJECTS AND ADVANTAGES

Accordingly, we claim the following as our objects and advantages of the invention: to provide a bone gauge which enables a surgeon to quickly, precisely and conveniently measure the depth of holes in a bone, to provide an instrument with more than one element to contact and define the location of the distal bone wall, to provide an instrument with which a surgeon can quickly, easily and precisely determine when the zero index of the instrument is lined up with the edge of the hole thru the distal wall, to provide an instrument with which a surgeon can access any reasonably desired location on or in a human body, to provide an instrument which is reasonably sized, and which is not too heavy, such that a surgeon can use it conveniently, to provide an instrument which has a reasonable number of parts while offering the advantages of an expanding zero index which positively engages the edge of the distal bone wall without the chance of slipping off, and therefore precisely aligns the scale zero index with that which is being measured, to provide an instrument which is used alone, without Xray, or additional equipment.

Readers will find further objects and advantages of the invention from a consideration of the ensuing description and the accompanying drawings.

DRAWING FIGURES

Drawing Reference Numerals

Figure 1:
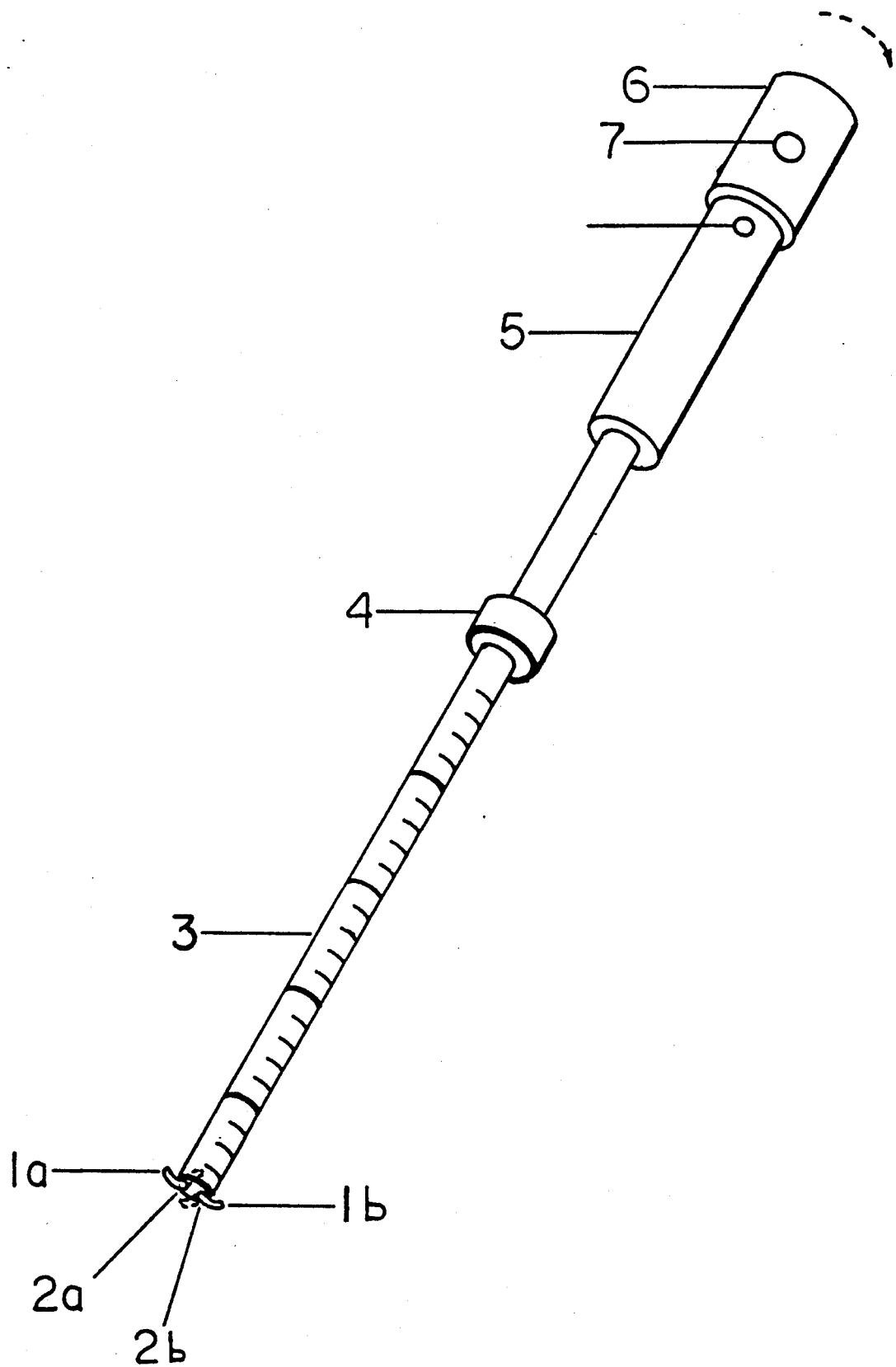
FIG. 1 is a perspective view of a preferred embodiment of a depth gauge, according to the invention.

1: zero index whiskers
2: end bearing holes
3: scale tube
4: scale marker
5: handle
6: knob
7: clamping screw
8: rotation limiting screw

DESCRIPTION OF THE PREFERRED EMBODIMENT

Referring to the drawings, FIG. 1 shows a depth gauge of the preferred embodiment of the invention. The device consists of a scale tube 3 having end bearing holes 2a and 2b which act as bearings and thru which protrude zero index whiskers 1a and 1b. This zero index "expands or contracts" in a controllable fashion, by radial rotation about their linear axes of the whisker wires, 1a and 1b, causing the short right angle portions thereof to describe arcs and thus planes normal to the scale tube but remaining fixed in the axial dimension (linear axis) according to the need respectively to either form a positive index stop, or to fit inside the dimensional envelope of the scale tube, during insertion and removal from a hole in the bone. A graduated measuring scale is printed on the scale tube. A scale marker 4 can be slidably located on the scale tube, thus marking the dimension. A handle 5 affords a way to grasp the gauge and a knob 6 controls the zero index whiskers.

Figure 2:
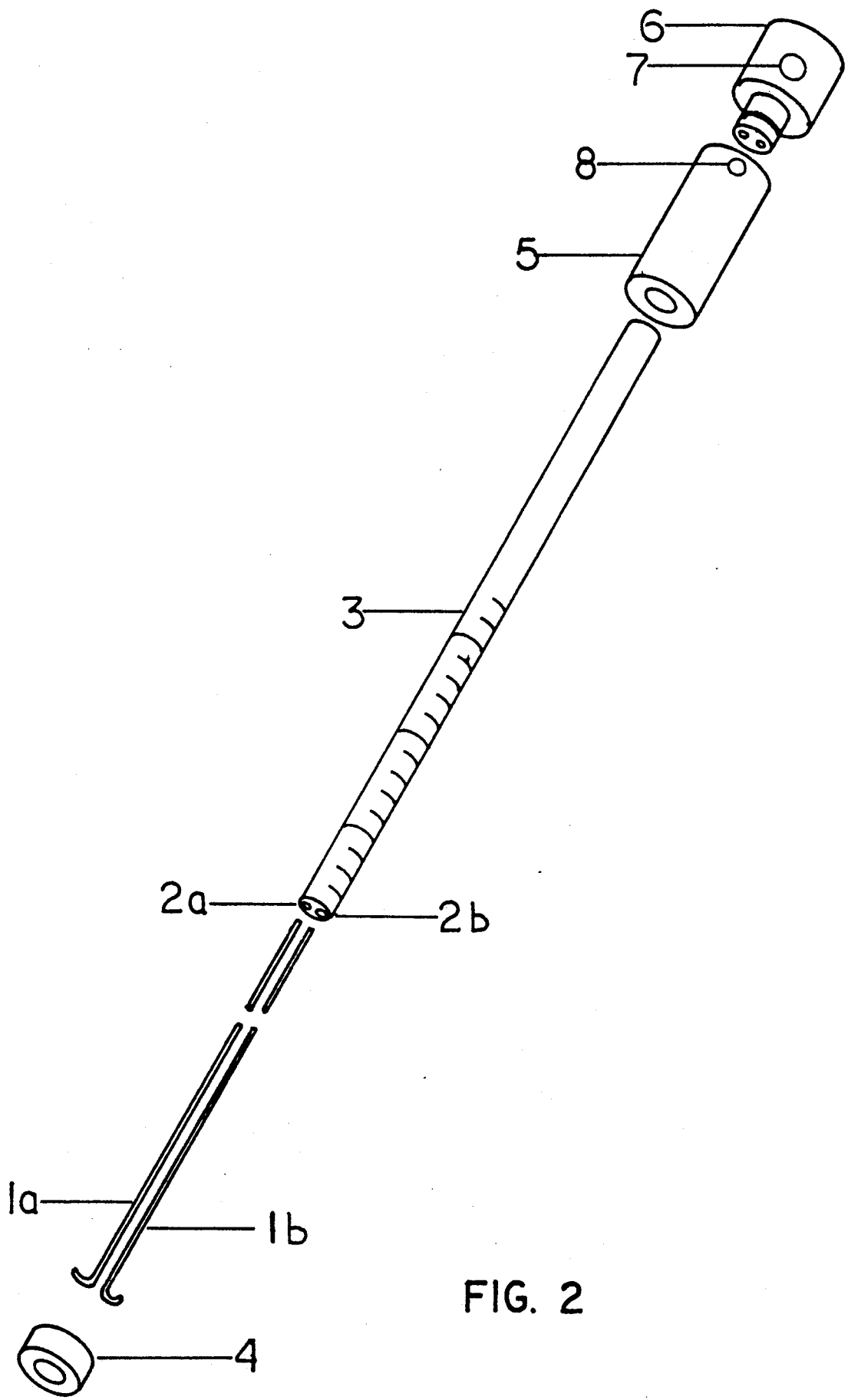
FIG. 2 is an exploded view of the depth gauge of FIG. 1.
Figure 3:
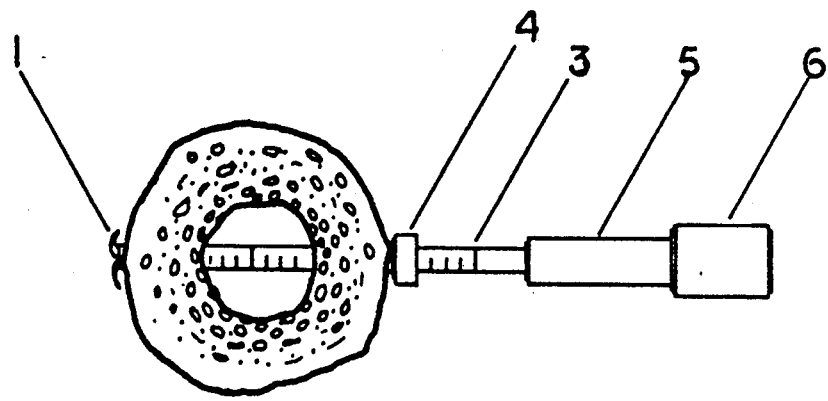
FIG. 3 is a view of the depth gauge of FIG. 1, inserted into a bone, with the zero index expanded, and the scale marker set to the measuring position.

FIG. 2 shows details of construction of the depth gauge of FIG. 1. FIG. 2 shows how the zero index whiskers 1a and 1b are clamped in holes in the knob 6, pass through the handle 5, through the scale tube 3, and out through the holes 2a and 2b in the end of the scale tube. The whiskers 1a and 1b are then bent through a norminal right angle and terminated, so that they do not protrude beyond the diameter of the scale tube when rotated into a "contracted" position. The bent ends are further shaped so as to fit smoothly inside the end profile of the scale tube. The ends have a slight hook shape, but are everywhere smoothed and polished to eliminate sharp edges. Since the whiskers 1a and 1b are quite flexible radially over their length, but not very flexible torsionally, and since they are secured by clamping screw 7 in the knob 6, then, as the knob is rotated, the whiskers also rotate about their linear axes, and the terminal ends describe an arc and thus a plane normal to the linear axis of the scale tube 3. This is the method of causing the zero index to "expand" (terminal ends point outwardly away from the centerline of the scale tube 3), or "contract" (terminal ends point inwardly toward the centerline of the scale tube.) This motion is exclusively normal to the linear axis of the scale tube.

The scale tube 3 is a length of stainless steel tubing, with the distal end closed by a short stainless steel plug. The diameter is selected such that it is an easy slip fit into the hole in the bone. The scale is printed and calibrated with circumferential lines at 10 mm increments, and short lines at 2 mm increments. Beginning at 10 mm, between each 10 mm line, an appropriate numeral indicates the decade. The scale tube is press fitted into the handle.

The scale marker 4 is made of plastic. See FIG. 4. It is disk shaped, and has a complex inner diameter which effectively exerts a spring pressure onto the scale tube 3. When assembled, the marker inner diameter expands elasticly over the scale tube. This spring action maintains adequate force on the scale tube 3 such that the marker 4 remains where the surgeon positions it. This "marks" the measurement.

The handle 5 is a round rod of stainless steel, externally diamond knurled to facilitate grasping. It is internally bored thru and counterbored on one end to receive the press fittment of the scale tube 3. On the other end it is counterbored with a bearing fit for the pilot of the knob 6. Radially, into this counterbore protrudes a dog point screw 7 which acts to retain the knob into the handle, and also to limit the axial rotation of the knob 6 in relation to the handle 5. This affords a positive stop to rotation and therefore defines the limits of expansion and contraction of the zero index.

The knob 6 is a round rod of stainless steel, diamond knurled on its outer diameter to enhance grip. The knob has a pilot on one end which fits into a counterbore in the handle 5. The knob is drilled partially through in two places on the pilot end, which holes are for the insertion of the whisker wires 1a and 1b. The knob 6 is cross drilled into the two whisker holes, to accept a screw 7 which effects a clamp for the whisker wires.

Operation

Having drilled a hole in the bone pieces, the surgeon grasps the bone depth gauge, noting that the knob 6 is rotated fully anticlockwise, which insures that the zero index whiskers 1a and 1b are fully contracted. He inserts the scale tube 3 into the hole in the bone, until he assumes that the zero index is nearing or has just passed the distal end of the hole. The surgeon then attempts to rotate the knob clockwise. If the zero index has indeed cleared the distal end of the hole, the zero index will expand freely, and thus the knob will rotate without resistance. If, however, the zero index is constrained by the walls of the hole, then the knob will not rotate easily, and the surgeon will insert the scale tube 3 further, while attempting to rotate the knob clockwise. As the zero index clears the distal bone wall, the zero index will expand, and the knob will rotate until stopped by the limiting screw 7. At this time, the surgeon withdraws the bone depth gage until it stops, because the zero index has come into intimate contact with the distal bone wall. The surgeon may then read the scale 3, or he may alternatively slide the scale marker 4 against the proximal bone wall, rotate the knob 6 anticlockwise and withdraw the bone depth gage from the hole. The scale marker 4 will stay in position on the scale, marking the measurement of the hole.

It will be appreciated that the instrument herein described may be quite small, the length only somewhat greater than the diameter of the bone being measured. The operation of the zero index is radial only, it has no linear extension. This allows the instrument to be short enough to access any required location. The diameter of the scale tube is smaller than the hole being measured and the diameter of the handle and knob only large enough to afford an adequate and comfortable finger grasp. The weight of the resultant instrument is negligible. The operation of the instrument requires only rotating the the knob and the marker requires only a finger "flick" to slide it against the proximal wall of the bone. The invention has five specialized parts, three of which move, and is, therefore cost effective both to manufacture and to maintain.

While the above description contains many specificities, the reader should not construe these as limitations on the scope of the invention, but merely as exemplifications of preferred embodiments thereof. Those skilled in the art will envision many other possible variations within its scope. For example, skilled artisans will readily be able to change the dimensions and shapes of the various embodiments. The scale tube could be of any diameter, as dictated by the hole size, and any length, as dictated by the bone size. They will also be able to make the bone depth gauge of alternative materials, such as plastics or other metals. They can make the scale tube flexible. They can provide for interchangeable scale tubes. They can change the number of zero index elements. They can design the zero index whiskers to articulate along the scale tube axis about an axis which is 90 degrees to the scale tube axis. They can power the zero index whiskers with a rod and cam. They can mount the zero index whiskers on pivots or flexures. The scale could be at the top of the device, above or integral with the knob. The scale tube could telescope thru the handle. An additional scale could be provided and used to measure the length of the device projecting unused from the bone. An additional scale could be inverse, or directly read, such that one could directly read the amount of tube engaged in the bone, from a scale arithmetically calculated and marked. Accordingly, the reader is requested to determine the scope of the invention by the appended claims and their legal equivalents, and not by the examples which have been given.

I claim:

1. An instrument for measuring the depth of a hole comprising:
   means defining a tubular body adapted to pass into and through a hole,
   zero index means at one end of said body said zero index adapted to expand and contract controllably exclusively in a plane normal to the axis of said tubular body,
   a scale means to measure the length of said tubular body which is inserted into a hole,
   a marker means associated with said scale means, frictionally restrained to stay where it is placed,
   a handle means attached to the opposite end of said body from said zero index, and
   actuating means attached to said handle, operatively connected with said zero index providing means whereby said zero index is expanded and contracted,
   said zero index being adapted to pass through said hole when contracted but when expanded, to engage distal edge of hole, thereby effecting alignment of zero index with distal wall of said hole such that closest interpolation of scale is an accurate reading of hole depth.

2. The instrument of claim 1 wherein said means defining a tubular body comprises a tube closed at the distal end by a plug containing said zero index means control holes.

3. The instrument of claim 2 wherein said zero index is a single element or a plurality of elements the plane of which is substantially at a right angle to the axis of said tubular body and operatively connected with said actuating means, whereby said element(s) extend(s) radially beyond said tubular body when said zero index is expanded but fit within the projected diameter of said tubular body when said zero index is contracted.

4. The instrument of claim 3 wherein said scale is printed on said tubular body.

5. The instrument of claim 4 wherein said actuating means is a knob which is borne by the end of the handle means and connected operatively to said zero index element(s) by torsional means such that rotation of said knob about the linear axis of said tubular body causes expansion and contraction of said zero index.

6. A depth gauge for measuring the depth of holes in bone comprising:
   a tubular body adapted to pass into and through a hole in bone,
   zero index means at one end of said tubular body adapted to expand and contract controllably exclusively in a plane normal to the axis of said tubular body,
   a scale means to measure the length of said tubular body which is inserted into said hole,
   a marker means associated with said scale means frictionally restrained to stay where it is placed,
   a handle means attached to said tubular body at the opposite end of said zero index,
   actuating means attached to said handle, operatively connected with said zero index providing means whereby said zero index is expanded and contracted,
   said zero index being adapted to pass through said hole when contracted, but when expanded to engage distal edge of hole, thereby effecting alignment of said zero index of said tubular body with distal wall of said hole such that closest interpolation of said scale is an accurate reading of hole depth.

7. The instrument of claim 6 wherein said tubular body is closed at said zero index end by a plug containing a hole or holes for the control of said zero index.

8. The instrument of claim 7 wherein said zero index is a single element or a plurality of elements the plane of which is substantially at a right angle to the axis of said tubular body, and operatively connected with said operating means, whereby said element(s) extend(s) radially beyond said tubular body when said zero index is expanded but fit within the projected diameter of said tubular body when said zero index is contracted.

9. The instrument of claim 8 wherein said scale is printed on said tubular body.

10. The instrument of claim 9 wherein said actuating means is a knob which is borne by the end of said handle means and connected operatively to said zero index element(s) by torsional means such that rotation of said knob about the linear axis of said tubular body causes expansion and contraction of said zero index.

11. The instrument of claim 10 wherein said marker means is slidably mounted on said tubular body and frictionally restrained to stay where it is placed.

* * * * *